(12) United States Patent
Bollenbach et al.

(10) Patent No.: US 7,758,550 B2
(45) Date of Patent: Jul. 20, 2010

(54) INJECTION DEVICE WITH A TIME-CONSTANT DELIVERY SIGNAL

(75) Inventors: Markus Bollenbach, Bern (CH);
Patrick Hostettler, Hasle-Ruegsau (CH); Daniel Kuenzli, Langendorf (CH); Ralph Mosimann, Rothrist (CH); Ursina Streit, Bern (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 12/052,917

(22) Filed: Mar. 21, 2008

(65) Prior Publication Data

US 2008/0262438 A1 Oct. 23, 2008

(30) Foreign Application Priority Data

Mar. 22, 2007 (DE) .................. 10 2007 013 838

(51) Int. Cl.
*A61M 5/00* (2006.01)
(52) U.S. Cl. .................. 604/207; 604/135; 604/506
(58) Field of Classification Search .................. 604/130, 604/131, 134–137, 156, 157, 118, 121
See application file for complete search history.

(56) References Cited

U.S. PATENT DOCUMENTS 2,585,815 A * 2/1952 McLintock .................. 604/209
5,104,380 A * 4/1992 Holman et al. .............. 604/117
2003/0130619 A1 * 7/2003 Safabash et al. ............ 604/136
2006/0258989 A1 11/2006 Kirchhofer

FOREIGN PATENT DOCUMENTS

DE 10015616 A1 10/2004

* cited by examiner

*Primary Examiner*—Kevin C Sirmons
*Assistant Examiner*—Larry R Wilson
(74) *Attorney, Agent, or Firm*—Dorsey & Whitney LLP; David E. Bruhn, Esq.

(57) ABSTRACT

An injection device for administering a liquid product, the device including a drive mechanism, an engaging member and a catch including a number of latching elements, wherein at least one of the engaging member and the number of latching elements is relatively moveable to the other to generate a haptic and/or acoustic signal comprising a number of discrete signals during a relative movement, wherein one of the catch and the engaging member is coupled to the drive mechanism and the drive mechanism generates a variable drive speed during the relative movement, and wherein the latching elements are a distance ($x_0$; $x_0-\Delta x$) from each other such that a time interval between each of the number of discrete signals is constant. A method for generating a haptic and/or acoustic signal in use of an injection device is encompassed.

24 Claims, 13 Drawing Sheets

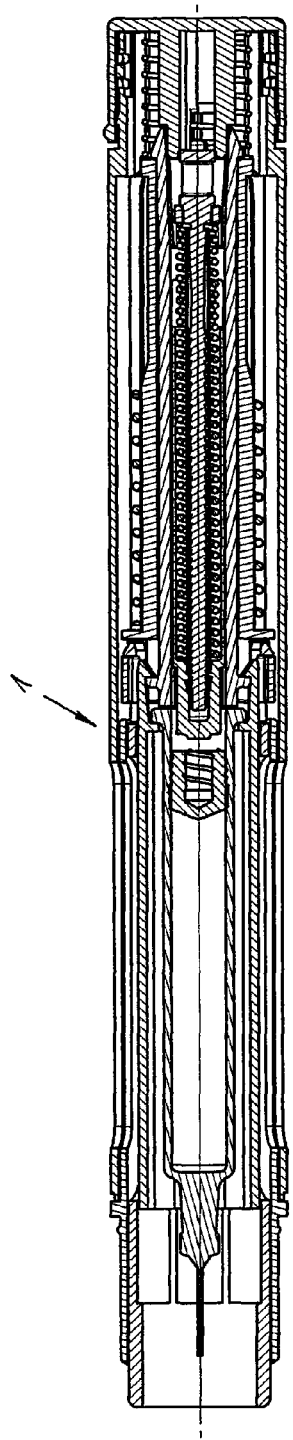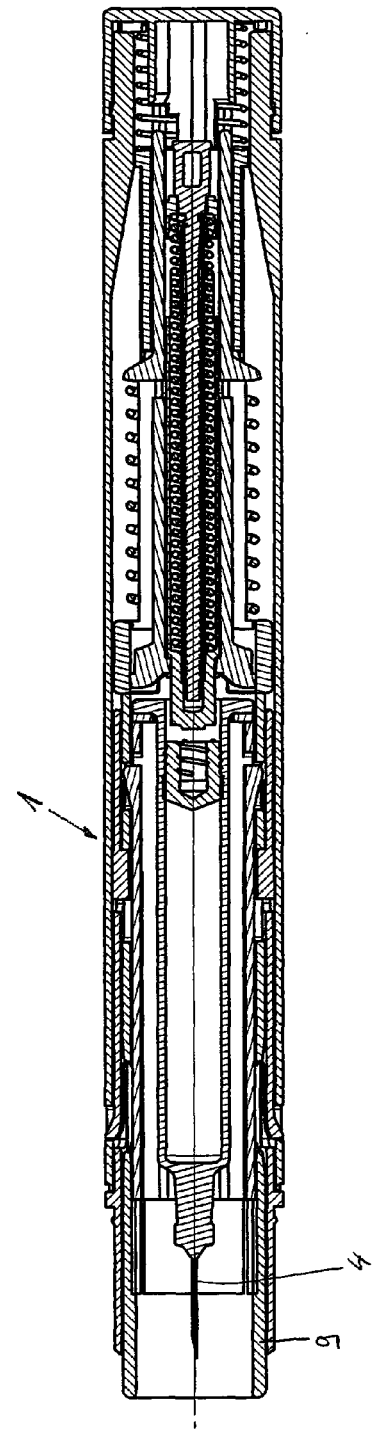
Figure 2a
Figure 2b

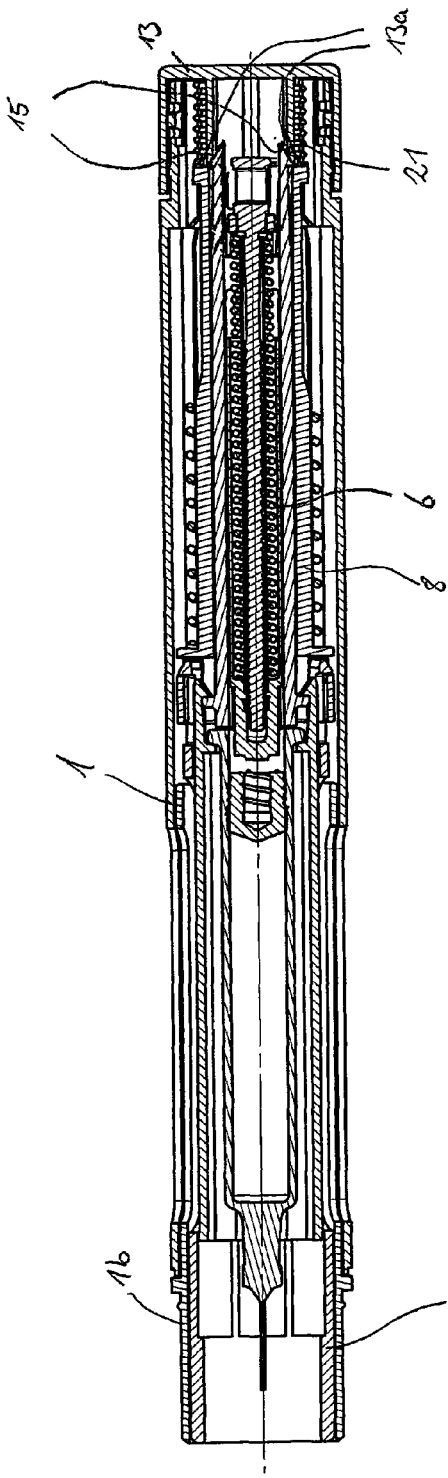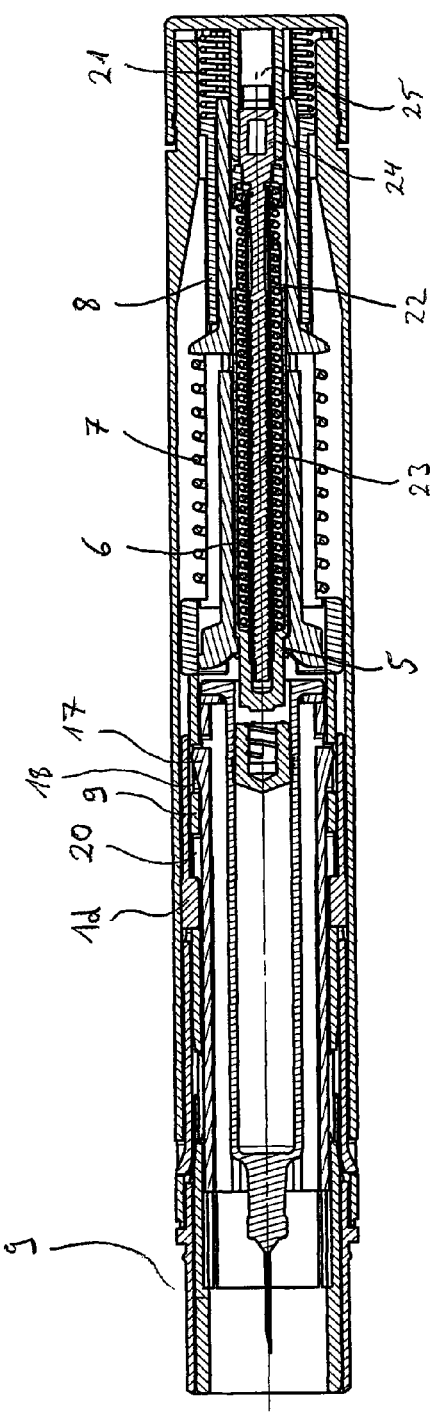
Figure 4a                    Figure 4b

INJECTION DEVICE WITH A TIME-CONSTANT DELIVERY SIGNAL

CROSS-REFERENCE TO RELATED APPLICATIONS

This application claims priority to German Application No. DE 10 2007 013 838.7 filed on Mar. 22, 2007, the content of which is incorporated in its entirety herein by reference.

BACKGROUND

The present invention relates to devices for injecting, administering, infusing, dispensing or delivering a substance, and to methods of making and using such devices. More particularly, the invention relates to an injection device for administering a liquid product, e.g. a medicine.

In known injection devices, a liquid product situated in a product container is delivered by a force which acts on a piston arranged in the product container such that it can be shifted. The force is transmitted via the piston onto the liquid, such that the latter is delivered via an opening in the product container, wherein the piston is generally shifted in the direction of the opening. Biased springs which act on the piston are often used to generate the force. The problem with such biased springs is that the spring force decreases as the spring relaxes, in accordance with the path or travel. To be able to determine, in the case of injection devices, whether a product is in the process of being delivered or has been completely delivered, signals can be generated during the advancing movement of the piston, for example by a relative movement being performed between a catch and an engaging element, such that clicking sounds are emitted as the catch is crossed. However, the emitting of clicking sounds can be misleading for users of such devices, since the spring force, which is variable over the spring path, causes irregularities in the emission of clicking sounds.

SUMMARY

It is an object of the present invention to provide an injection device and a signalling device or feature for injection devices by which a user of the device is better able to monitor and/or ascertain procedures, operations or movements being performed in the interior of the injection device.

In one embodiment, the present invention comprises an injection device for administering a liquid product, the device comprising a drive mechanism, an engaging member and a catch comprising a number of latching elements, wherein at least one of the engaging member and the number of latching elements is relatively moveable to the other to generate a haptic and/or acoustic signal comprising a number of discrete signals during a relative movement, wherein one of the catch and the engaging member is coupled to the drive mechanism and the drive mechanism generates a variable drive speed during the relative movement, and wherein the latching elements are a distance ($x_0$; $x_0-\Delta x$) from each other such that a time interval between the number of discrete signals is constant. A method of producing the haptic or acoustic signal is encompassed.

In one embodiment, an injection device in accordance with the present invention may be adapted to deliver only one product or dose of a product from a product container. The device may be disposable or not. In some preferred embodiments, an injection device in accordance with the present invention may be a so-called auto-injector, in which a mechanism is provided which enables the needle to be automatically injected and the product to be subsequently delivered.

In some embodiments, an injection device in accordance with the present invention comprises a catch which comprises at least three latching elements. In some preferred embodiments, a plurality of latching elements, i.e. more than three latching elements, such as for example 40 or even up to 100 latching elements, are provided and, in theory, it is also possible to provide far more than 100 latching elements. In some preferred embodiments, the latching elements are sequential in the longitudinal direction of the device, i.e. the direction in which an engaging member can be moved relative to and on the catch. During the movement relative to the catch, the engaging member is in an engagement with the catch or its latching elements. Each time the latching elements are crossed, i.e. each time the engaging member is moved over the latching elements, a haptic and/or acoustic signal is generated. A haptic signal, which the user of the device can sense via the hand gripping or holding the device, can, for example, be a tactile signal. The acoustic signal can be perceived via the audio perception of the user of the device. In principle, it is possible to generate either a haptic signal or an acoustic signal. In some preferred embodiments, the signal can be perceived both haptically and acoustically, such that it can be perceived via different sensory organs.

In some preferred embodiments, the engaging member can, for example, be an elastically arranged cam. The engaging member is elastically connected via an elastic arm to another component. It would also be conceivable to hold the engaging member in an engagement with the catch via a separate spring or other elastic spring element. The engaging member is biased via the elastic arrangement, such that it is held in contact with the catch or latching elements.

In some embodiments, the latching elements can be projections or cavities, which can be crossed or traversed by the engaging member. The latching elements can be tooth-shaped, e.g. serrated tooth-shaped, projections. The latching elements can also be pockets, holes or breaches. The engaging member and/or the latching elements are shaped such that the latching elements can be crossed by the engaging member in at least one direction. If, for example, a latching element is formed in the shape of a serrated tooth-shaped projection, it is desirable if the engaging member can only cross the latching elements in one direction. When the engaging member moves in the other direction, i.e. the opposite direction, a relative movement between the catch and the engaging member is blocked, locked or prevented. In principle, shapes other than a serrated tooth shape are also conceivable to obtain an engaging member which can only move in one direction.

In some embodiments, as the engaging member moves along the catch, the engaging member is deflected e.g. outwardly and/or gradually, wherein the elastic arrangement of the engaging member is biased. The latching elements comprise an edge, whereby, due to its biased elastic arrangement, the engaging member is moved abruptly toward the catch once it passes said edge, such that it impacts on the catch. This impact generates the haptic and/or acoustic signal. In some embodiments, this signal is or causes a perceptible shaking of the injection device and/or an audible clicking sound.

In some embodiments, to generate the relative movement between the catch and the engaging member, one of the catch and the engaging member, i.e. either the catch or the engaging member, is fixedly coupled, e.g. axially, to a driver or drive means. A drive speed of the drive means or engaging member, which is variable over the path, can be generated by the drive means. The drive speed is for example dependent on a drive force of the drive means which is variable over the path. Such a characteristic is exhibited by elasticity elements, such as springs. A spring can be understood to mean a rubber-elastic spring or a spring which obeys Hooke's law. A known example of a spring which obeys Hooke's law is a helical spring made of spring steel, plastic or other suitable material. A spring which obeys Hooke's law is characterised in that the ratio of the spring force to the spring extension is constant. In the case of a rubber-elastic spring, this ratio is not constant.

A random arrangement of the latching elements relative to each other, e.g. with regard to their spacing, would make it unclear to the user of the device what state the mechanism of the device is in. This could mislead the user of the device. In accordance with the present invention, signals are emitted at constant time intervals, i.e. the latching elements are crossed at constant time intervals. To this end, the latching elements have distances from each other such that the time intervals between the signals are constant. In particular, the variable drive speed and/or power of the drive means is taken into account when determining the distances. If the latching elements are arranged at equal distances from each other, the variable drive speed would cause the acoustic signals to be emitted at time intervals of differing lengths. For a drive means in accordance with the present invention in which the speed is increased, the distances between the latching elements increase accordingly, while for a drive means in accordance with the present invention in which the drive speed is reduced, the distances decrease. A signal is also understood to mean the combination of a plurality of individual signals which are repeated with the next signal. This can, for example, be a double click, wherein the time intervals until the next double click, from the next double click to the next double click but one, from the next double click but one to the next double click but two, etc. are decisive.

When, for example, a spring which obeys Hooke's law relaxes, a distance is traveled and the spring force linearly decreases, hence the speed of movement of the engaging member relative to the catch also decreases. Thus, in some embodiments of the present invention, the distances between the latching elements as measured in the movement direction are respectively shortened by a corresponding amount, such that the time intervals between the signals are constant.

In some embodiments, the signalling unit formed by the catch and the engaging member can advantageously be used to signal different movements of the mechanism of the injection device. Thus, for example, an injection procedure or movement of an injection needle can be signalled. Alternatively or additionally, as in some preferred embodiments, the delivery of the product can also be signalled in this way. The drive means can be coupled to a piston of a product container, such that the piston can be moved in an advancing direction.

For signalling the injection procedure, in some preferred embodiments, the injection needle can be moved in the advancing direction by the drive means, i.e. if the injection needle is correspondingly connected directly or indirectly to the drive means. The injection needle can be connected to the drive means via a product container on which the injection needle is arranged. The piston is moved, together with the product container, by the drive means in the advancing direction, i.e. the injecting direction of the needle. To this end, the product container can be mounted such that it can be moved in a casing of the device. The product container can be dimensioned and arranged with the needle such that the needle protrudes or extends from the distal end of the injection device during an advancing movement, i.e. an injection movement. Using such an arrangement, the user of the device can determine when the injection procedure is finished from the signals emitted, e.g. from the number of signals emitted or from the end of the emission of signals.

In a preferred embodiment, in which the signalling unit serves to signal the delivery of the product, the piston of the product container is connected to the drive means such that the piston can be moved by the drive means relative to the product container in the advancing direction, i.e. in the delivery direction. In embodiments in which an injection procedure is performed and product delivered, the advancing movements required for injecting and delivering the product can be performed by a common drive means. A common catch can accordingly be provided, along which the engaging element is moved during both injecting and delivery. in some embodiments, the catch can comprise different sections, e.g. one section for the injection movement and one for the delivery movement. The ratio of the distances between the latching elements in one section to that of the distances between the latching elements in the other section can be such that constant intervals of a first duration are generated in said one section and constant intervals of a second duration, different from the first duration, are generated in the other section. It is also possible to provide one section, e.g. the section for the injection procedure, without any latching elements.

In some preferred embodiments, a damping element is coupled to the drive means such that the drive force of the drive means is damped, e.g. with a damping action which is strong enough that creeping, including an aperiodic borderline case or creep, occurs. Creeping occurs when the damping action $\delta$ is greater than the natural frequency $\omega_0$ of the spring. The aperiodic borderline case occurs when $\delta=\omega_0$, wherein the product is aperiodically delivered most quickly in this case. Preferably, $\delta \geq \omega_0$, such that the spring is asymptotically relaxed. In some preferred embodiments, the damping element is formed by or from the product container with the liquid product contained in it, which can be discharged from the product container via an opening.

In some embodiments, the engaging member can be formed on a carriage which is coupled to the drive means, e.g. via a piston rod which acts on the piston. The engaging member is elastically connected, e.g. in one piece, to the carriage via an elastic arm. The drive member can act on the piston rod and can be supported on it. The carriage can latch, axially fixed, to the piston rod. It is also conceivable for the piston rod and the carriage to be formed in one piece or for the engaging member to be directly attached to or formed on the piston rod. The engaging member is thus slaved in the movement of the piston rod. The carriage can be arranged in a groove, relative to which it can be moved. The latching elements can be arranged in the groove. The latching elements can be arranged on a flank of the groove, such that the latching elements project from the flank or extend into the flank.

In a preferred embodiment, the catch is formed on a sleeve, e.g. a functional or operational sleeve associated with or involved in the operation of the injection device, which surrounds the engaging member. The sleeve can comprise the groove in which the catch is arranged. If they project from a side or flank of the groove, the latching elements can point in the circumferential direction of the sleeve. The functional sleeve can comprise a blocking element or lock which is in engagement with the piston rod such that a movement of the piston rod relative to the functional sleeve is blocked. This engagement is releasable, such that the piston rod can be released for a delivery movement.

In another embodiment, the catch can be arranged on a rod-shaped element surrounded by a sleeve on which the engaging member is formed. This forms a telescopic structure which generates the cited signals when it is pulled apart. In some preferred embodiments, the latching elements point radially outward and the engaging member projects radially inward. The latching elements can be annular projections which surround the circumference of the rod-shaped element. The latching elements can be truncated cones which are arranged in a row in the longitudinal direction and exhibit approximately the same diameter at their base area but different heights, which determine the distance between the latching elements. The rod-shaped element is axially and fixedly connected to a casing, an element fixed to the casing or a switch sleeve which can be moved relative to the casing. The sleeve surrounding the rod-shaped element is also fixedly connected, such as for example latched, axially to the piston rod. The delivery spring is supported on the casing, on an element fixed to the casing and/or on the switch sleeve. In some preferred embodiments, the advancing spring serving as the drive means and the rod-shaped element are supported on the switch sleeve. A head of the rod-shaped element can be supported on the switch sleeve, such that it can be moved in the proximal direction and is axially fixed in the distal direction. The head can be accommodated in a guide, such that the rod-shaped element drawn out of the sleeve can be shifted in the proximal direction of the injection device. The advantage of this is that the injection needle can be slid back into the casing, such that the risk of injury to the user and third parties is reduced.

In yet another embodiment, the catch can be arranged on the piston rod and the engaging member can be arranged on a sleeve surrounding the piston rod, e.g. the functional sleeve. Since the piston rod is moved relative to the functional sleeve during the delivery movement, the signalling unit can also be arranged there. In this embodiment, holes may serve as latching elements, but projections are also possible.

The present invention also relates to a method for generating a haptic and/or acoustic signal in an injection device, wherein an engaging member is moved relative to and on a catch which comprises at least three latching elements, a drive speed which is variable over the path is generated by a drive means coupled to one of the catch and the engaging member, and a haptic and/or acoustic signal is generated whenever the latching elements cross or are crossed. In some embodiments, the present invention comprises emitting the signals at constant time intervals. The constant time intervals are generated when the latching elements, which have a distance from each other such that the time intervals between the signals are constant, cross or are crossed.

BRIEF DESCRIPTION OF THE DRAWINGS

FIG. 1, including FIGS. 1a and 1b, is a sectional representation of an embodiment of an injection device in accordance with the present invention, with a cap fitted, wherein FIG. 1b is a view rotated by 90° about the longitudinal axis relative to FIG. 1a;

FIG. 2, including FIGS. 2a and 2b, is a sectional representation of the injection device with the cap removed, wherein FIG. 2b is a view rotated by 90° about the longitudinal axis relative to FIG. 2a;

FIG. 3, including FIGS. 3a and 3b, is a sectional representation of the injection device in an activated state, wherein FIG. 3b is a view rotated by 90° about the longitudinal axis relative to FIG. 3a;

FIG. 4, including FIGS. 4a and 4b, is a sectional representation of the injection device in a triggered state, wherein FIG. 4b is a view rotated by 90° about the longitudinal axis relative to FIG. 4a;

FIG. 5, including FIGS. 5a and 5b, is a sectional representation of the injection device in an injected state, wherein FIG. 5b is a view rotated by 90° about the longitudinal axis relative to FIG. 5a;

FIG. 6, including FIGS. 6a and 6b, is a sectional representation of the injection device in a delivered state, wherein FIG. 6b is a view rotated by 90° about the longitudinal axis relative to FIG. 6a;

FIG. 7, including FIGS. 7a and 7b, is a sectional representation of the injection device in a state in which the injection device has emitted a clicking sound signalling the end of delivery, wherein FIG. 7b is a view rotated by 90° about the longitudinal axis relative to FIG. 7a;

FIG. 8, including FIGS. 8a and 8b, is a sectional representation of the injection device in which a retraction of the injection needle is activated, wherein FIG. 8b is a view rotated by 90° about the longitudinal axis relative to FIG. 8a;

FIG. 9, including FIGS. 9a and 9b, is a sectional representation of the injection device in an end state, wherein FIG. 9b is a view rotated by 90° about the longitudinal axis relative to FIG. 9a;

DETAILED DESCRIPTION

Figure 1A:
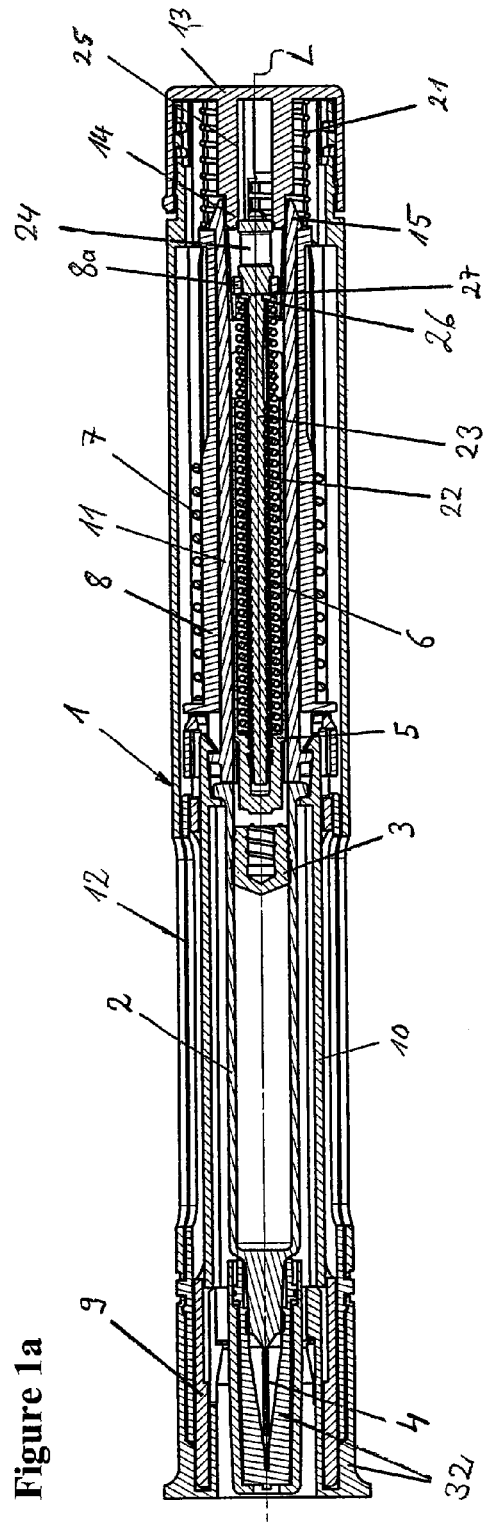

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc. Unless stated otherwise, identical reference characters refer to the same parts.

FIGS. 1-9 show one exemplary preferred embodiment of an injection device in accordance with the present invention. Referring to FIGS. 1a and 1b, the injection device comprises a casing 1 consisting of a proximal (rear) casing part 1a and a distal (forward) casing part 1b which is axially and fixedly connected to the proximal casing part 1a by a latching connection 1c. The latching connection 1c is formed from or by a window or opening contained in or associated with the proximal casing part 1a, into which an elastic tab formed or carried by the distal casing part 1b snaps.

A product container 2 is accommodated in the casing 1, on the distal end of which an injection needle 4 is situated for delivering a liquid product contained in the product container 2. The proximal end of the product container 2 comprises a shifting piston 3 which, when moved relative to the product container 2 and in the direction of the injection needle 4, delivers the product, for which reason this may also be referred to as a delivery movement. The product container 2 is accommodated in the device such that it can be shifted in the distal direction, such that the injection needle 4 protrudes from the distal end of the injection device. This may therefore be referred to as an injection movement. The product container 2 is axially and fixedly connected to a holder 10 for the product container 2. The casing 1, e.g. its distal and proximal casing parts 1a, 1b, comprise a viewing window 12 through which the user of the injection device can view the product container 2. The holder 10 surrounds the product container 2 in the shape of a sleeve, such that it either comprises a viewing window itself or, as in this example, comprises a transparent material, to enable the container 2 to be viewed. The product container 2 is axially and fixedly connected to a functional sleeve 11 arranged proximally (rearwardly) relative to it by a clamp formed at the proximal end of the holder 10. The proximal end of the product container 2 comprises a radially projecting collar which is encompassed by the clamp. The functional sleeve 11 also comprises a radially projecting collar at its distal end, which is also enclosed by the clamp. The product container 2, the functional sleeve 11 and the holder 10 are thus axially and fixedly connected to each other, such that they can be moved as a single part. This combination is referred to in the following as the advancing structure.

The functional sleeve 11 surrounds a piston rod 5 which can act on the piston 3 in order to deliver product. The piston rod 5 comprises a sleeve-shaped part which surrounds an advancing spring 6, wherein the advancing spring 6 is distally supported on the piston rod 5 and proximally supported on a switch sleeve 8, in or on a socket 8a formed on it.

A signalling unit is arranged on or associated with the piston rod 5, using which a haptic and/or acoustic signal, in some preferred embodiments at least three or more haptic and/or acoustic signals, can be generated for an injection procedure or operation and/or a delivery procedure or operation. The signalling unit comprises a catch rod 23 connected to the switch sleeve 8, and an engaging sleeve 22 which surrounds the catch rod 23 and is axially and fixedly connected, e.g. latched, to the piston rod 5. The engaging sleeve 22 comprises an engaging element 26 which engages with a groove 27 formed in or by the catch rod 23. The proximal end of the catch rod 23 comprises a head 24 which can be moved in the proximal direction in a sliding guide 25 formed by the activating element 13. The distal end of the head is in an engagement with a socket 8a formed by the switch sleeve 8, wherein the engagement prevents the head 24 and therefore the catch rod 23 from moving in the distal direction relative to the switch sleeve 8. The exact functionality of this arrangement is explained below with reference to FIGS. 10 and 11 which show in detail the signalling unit shown in FIGS. 1-9. The signalling unit from FIGS. 10 and 11 can alternatively be replaced with a different signalling unit in accordance with FIGS. 12 to 14 or with yet another signalling unit in accordance with FIGS. 15 and 16. The injection device shown in FIGS. 1-9 does not have to be significantly modified to accommodate these or other suitable embodiments of signalling units.

Figure 1B:
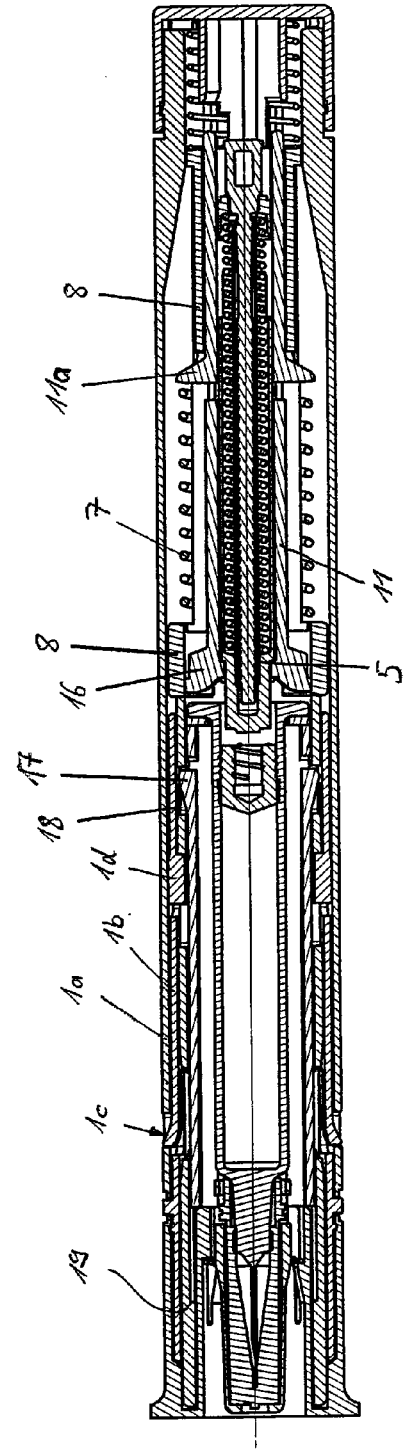

In the initial state of the injection device, shown in FIGS. 1a and 1b, the advancing spring 6 is biased such that it can advance the needle 4 and in particular the advancing structure (comprised of components 2, 10, 11) for an injection movement and can shift the piston 3 for a delivery movement. The functional sleeve 11 comprises a blocking element 16 on which a shoulder is formed which is directed radially inwardly and which, in the initial state, co-operates with a shoulder which projects radially outwardly and is formed at the distal end of the piston rod 5, such that the piston rod 5 is blocked against moving relative to the functional sleeve 11. The blocking element 16 is held in the engagement with the piston rod 5 by a surface of the switch sleeve 8 which points radially inwardly. In some preferred embodiments, the blocking element 16 is elastically connected, e.g. in one piece, to the functional sleeve 11 via an elastic arm. The elastic arrangement can be configured such that the blocking element 16 tends to move radially outwardly, wherein this is prevented by the surface of the switch sleeve 8 which points radially inwardly.

The proximal end of the functional sleeve 11 comprises at least one snapping element 15 which snaps into the switch sleeve 8 in the initial state to prevent the functional sleeve 11 and therefore the advancing structure from moving, hence the biased spring 6 cannot yet be relaxed and cannot yet move the advancing structure in the distal direction.

At the proximal end of its casing 1, the injection device comprises an activating element 13 which is arranged such that it is axially fixed but rotatable relative to the casing. The activating element 13 accommodates a restoring spring 21 which is distally supported on the proximal end of the switch sleeve 8 and proximally supported on the activating element 13. The restoring spring 21 has the task of charging the switch sleeve 8, and an operating sleeve 9 which acts axially on the switch sleeve 8, with a force which acts in the distal direction, such that the switch sleeve 8 and the operating sleeve 9 are pressed in the distal direction. The activating element 13 comprises an activation lock 14 which, in the switching states of the injection device shown in FIGS. 1a, 1b, 2a and 2b, grips behind the snapping element 15 such that the snapping element 15 is blocked, locked and/or secured against moving out of the engagement with the switch sleeve 8. This advantageously prevents the injection device from being inadvertently triggered. The activation lock can be moved out of the engagement with the snapping element 15 by rotating the activating element 13, for example by 90°, relative to the casing 1.

A retracting spring 7 which acts in the longitudinal direction of the device is distally supported on the switch sleeve 8 and proximally supported on the functional sleeve 11. As shown in this example, the retracting spring 7 surrounds the switch sleeve 8 and the functional sleeve 11. The retracting spring 7 is proximally supported on a collar 11a which is formed by the functional sleeve 11 and grips radially outwardly through a breach formed in the switch sleeve 8. In selected or particular switched positions, the retracting spring 7 can therefore generate a relative movement between the switch sleeve 8 and the functional sleeve 11. The retracting spring 7 is a compression spring which can move the functional sleeve 11 relative to the switch sleeve 8 in the proximal direction. The retracting spring 7 is not biased or is biased with only a small biasing force. When the injection device is in the state shown in FIGS. 1a and 1b, for example, the biasing force of the retracting spring 7 is smaller than the biasing force of the advancing spring 6.

The operating sleeve 9 is arranged distally relative to the switch sleeve 8 and such that it can be moved relative to the casing 1. The switch sleeve 8 and the operating sleeve 9 can reciprocally charge each other with a pressing force, and can be latched, operably coupled or connected to each other and thus shift each other. In order that it does not block the view onto the product container 2, the operating sleeve 9 also comprises a window in the region of the window 12. Alternatively, the operating sleeve 9 can be formed from a transparent material. In the initial state, the operating sleeve 9 is distally advanced beyond the distal end of the casing 1 by the restoring spring 21 via the switch sleeve 8. The distal end of the operating sleeve 9 serves to place the device onto an injection location on a patient.

The holder 10 comprises a switching cam 17 which engages with a cavity 18 in the operating sleeve 9 which can be a breach or opening as shown in this example. The switching cam 17 is elastically connected, e.g. in one piece, to the holder 10, for example via an elastic arm. The switching cam 17 is biased such that it tends to engage with the cavity 18 and/or move radially outwardly. The switching cam 17, which projects radially outwardly from the holder 10, distally comprises an oblique surface which assists in pressing the switching cam 17 out of the engagement with the cavity 18. The switching cam 17 also proximally comprises a contact surface which extends transversely or perpendicularly to the longitudinal direction and can pass into an axial abutment with the proximal boundary of the cavity 18, which prevents the switching cam 17 from moving out of the cavity 18.

The operating sleeve 9 comprises an axial abutment 19, against which the distal end of the holder 10 can abut at the end of an injection movement.

As shown in FIGS. 1a and 1b, a cap 32 is arranged on the distal end of the injection device and protects the interior of the injection device from contamination and keeps the needle 4 sterile. The cap 32 is removed before using the injection device, such that the needle 4 and the operating sleeve 9 are exposed, as shown in FIGS. 2a and 2b. The state of the injection device shown in FIGS. 2a and 2b differs from the state shown in FIGS. 1a and 1b in that the cap 32 has been removed.

The force exerted on the injection device when the needle cap 32 is removed is channeled via the holder 10 onto the functional sleeve 11, where it is transmitted via the snapper 15 onto the switch sleeve 8 which is supported on the operating sleeve 9. The operating sleeve 9 is in turn latched to the casing 1 via a projection 1d formed by the distal casing part 1, such that removing the cap 32 from the injection device does not exert any undesirable effect on the mechanism. In the switching state shown in FIGS. 2a and 2b, the operating sleeve 9 cannot be slid or can only be slid or moved very slightly into the distal end of the injection device, since this shifting movement is relayed to the snapper 15 via the switch sleeve 8, wherein the snapper 15 is prevented from moving in the proximal direction by the activating element 13.

Figure 3A:
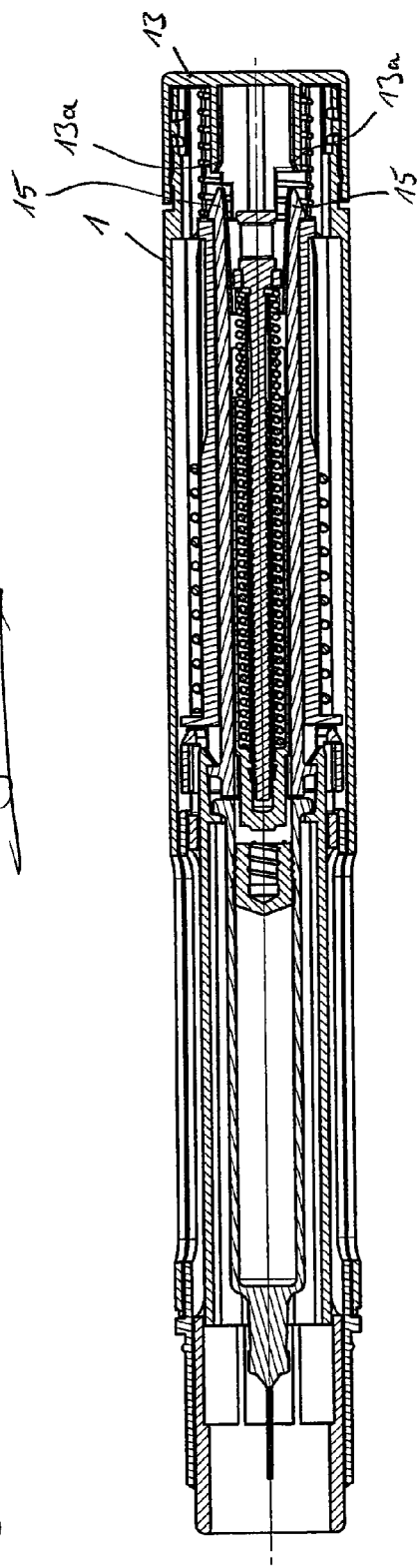
Figure 3B:
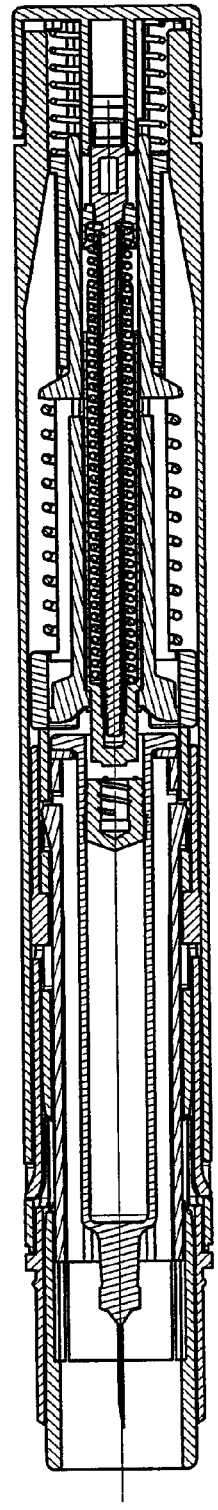

FIGS. 3a and 3b show the injection device in an activated state, i.e. in which the injection device can be triggered. The injection device is activated or unlocked by a rotational movement of the activating element 13 by, for example, 90°. This releases the snapping elements 15 for a movement directed radially inwardly, in that the activation lock 14 moves out of the engagement with the snapping elements 15 and is rotated. This creates space for the snapping elements 15 to be deflected inwardly. The activating element 13, like the snapping element 15, also comprises an activating cam 13a which is moved into axial alignment with the snapping element 15 by the rotational movement of the activating element 13. The snapping element 15 proximally comprises—and the activating cam 13a arranged proximally relative to it distally comprises—a contour which can deflect the snapping element 15 radially inwardly when the snapping element 15 is moved in an engagement with the activating cam 13. In this example, the contours are two inclined planes which slide off on each other.

To trigger the injection device, the user of the device places its distal end onto the injection location, which has usually been disinfected beforehand. This shifts the operating sleeve 9 relative to the casing 1 in the proximal direction, in some preferred embodiments until the distal end of the operating sleeve 9 is approximately flush with the distal end of the distal casing part 1b. The movement of the operating sleeve 9 slaves the switch sleeve 8 in the proximal direction, wherein the snapping elements 15 are pressed, radially inwardly, out of the engagement with the switch sleeve 8 by the activating cams 13a. As long as the snapping elements 15 are snapped into the switch sleeve 8, the elements of the advancing structure are also slaved or moved in the proximal direction by the movement of the operating sleeve 9 in the distal direction. Since the piston rod 5 is in a blocking engagement with the functional sleeve 11, the piston rod 5 is also slaved in the proximal direction. The signalling unit, which is accommodated in the piston rod 5, is also slaved in the proximal direction. The head 24 formed proximally on the catch rod 23 can slide along in the guide 25 formed by the activating element 13.

Since a relative movement between the activating sleeve 11 and the switch sleeve 8 is still not possible during this movement, neither the retracting spring 7 nor the advancing spring 6 are tensed or relaxed.

The force which the user of the device has to exert on the casing 1 for the operating sleeve 9 to be shifted in the proximal direction is substantially determined by the force of the restoring spring 21 against which the switch sleeve 8 and the operating sleeve 9 are moved. The spring 21 is a compression spring and is formed from a plastic material. Alternatively, it is of course also possible to use springs made of a spring steel material or other suitable material. The activating element 13 is axially attached to the casing 1 by an annular snapping connection with the casing. If the operating sleeve 9 is not pressed far enough onto the injection location, such that the snapping elements 15 are not released from the engagement with the switch sleeve 8, then the trigger mechanism, for example the switch sleeve 8 and the operating sleeve 9, is restored by the restoring spring 21 when the injection device is removed from the injection location.

As can be seen from FIG. 4b, the movement of the operating sleeve 9 in the proximal direction forms a blocking window 20 which is distally bounded by the casing 1, the projection 1d, and proximally bounded by the operating sleeve 9. Since there is no relative movement between the advancing structure and the operating sleeve 9 during the movement of the operating sleeve 9 in the proximal direction, the switching cam 17 remains in the cavity 18.

Once the snappers 15 have latched out of the engagement with the switch sleeve 8, the advancing spring 6 can be partially relaxed, which shifts the advancing structure in the distal direction, whereby the injection needle 4 protrudes beyond the distal end of the injection device. Since the functional sleeve 11 is moved relative to the switch sleeve 8 during this injection movement, the retracting spring 7 is compressed, i.e. tensed. The spring force of the advancing spring 6 is greater than the spring force of the retracting spring 7 during the entire injection procedure, i.e. also at the beginning and end of the injection procedure. The advantage of this is, for example, that the injecting force is reduced, which helps to avoid wear on the injection device.

Figure 5A:
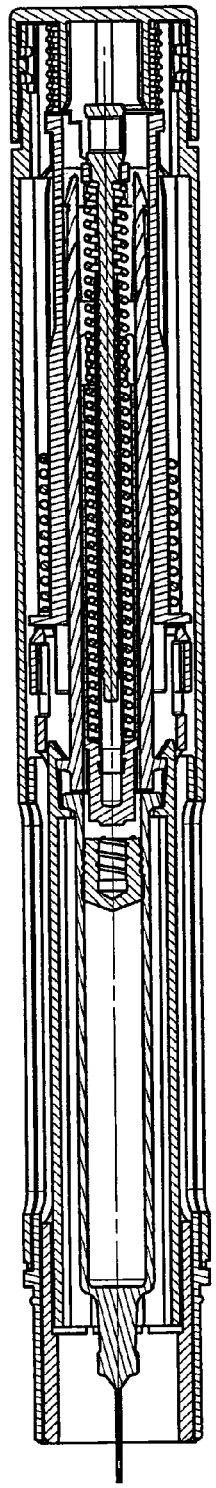
Figure 5B:
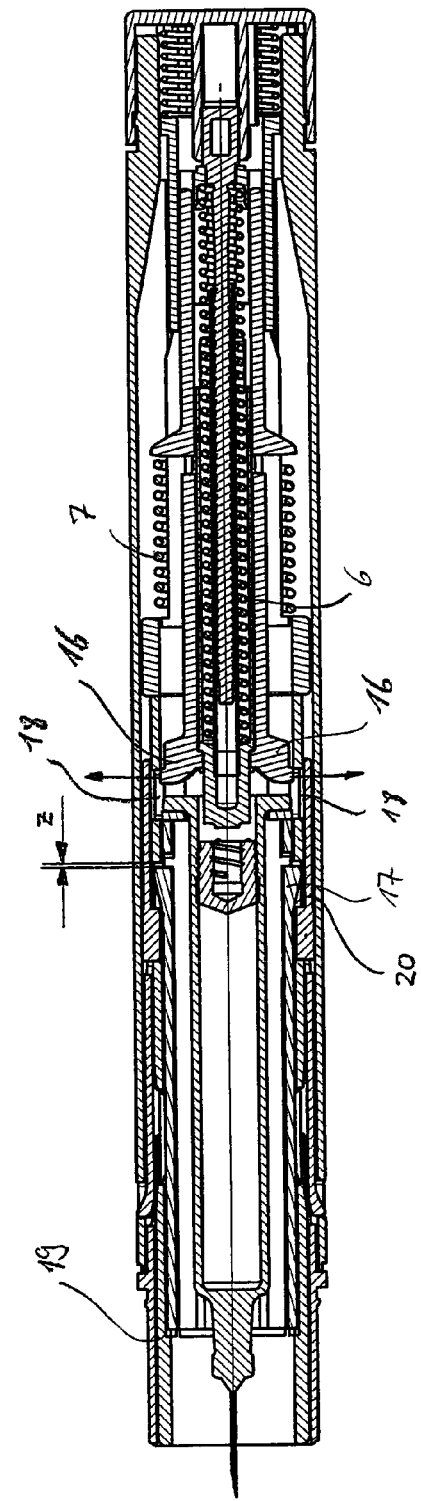

As can be seen from FIGS. 5a and 5b, which show the situation at the end of the injection procedure, the blocking element 16 engages with the cavity 18 in a movement which is directed radially outwardly, as indicated by the arrows in FIG. 5b. To facilitate this engagement, the blocking element 16 comprises a projection which is directed radially outwardly. The blocking element 16 fulfils a dual function. When the blocking element 16 latches into the cavity 18, the blocking element 16 simultaneously latches out of the piston rod 5 in the movement directed radially outwardly, such that the latter is released for a delivery movement. Conversely, the movement of the advancing structure axially, in the proximal direction, is blocked or prevented. This procedure decouples the advancing spring 6 from the retracting spring 7, i.e. the advancing spring 6 has no effect on the bias of the retracting spring 7 in this state. A delivery movement then follows, during which a time-constant clicking sound is emitted by the signalling unit and can also be sensed by the user of the device.

The user of the device does not sense any additional force caused by the injection procedure, which is collected by the snapping action between the operating sleeve 9 and the switch sleeve 8 and is not supported on the casing. The force for the injection procedure is channeled onto the collar of the product container 2 via the functional sleeve 11. The injection procedure is thus forcibly controlled, since the functional sleeve 11 advances the product container 2 until the end of delivery, and the piston rod 5 cannot deliver until the blocking elements 16 have engaged with the cavities 18. The injection movement is stopped by the abutment 19 on the operating sleeve 9.

During the injection movement, the switching cam 17 is pressed out of the engagement with the cavity 18, due to its distal design, by the distal boundary of the cavity 18 of the operating sleeve 9 and is shifted in the distal direction, such that it latches into the blocking window 20, as shown in FIGS. 5a and 5b. The blocking element 16, latched into the cavity 18, is in contact with the proximal boundary of the cavity 18. Since the blocking element 16 and the switching cam 17 are at a defined distance from each other due to their axially fixed arrangement, it is preferable if there is a commensurate or defined distance, e.g.—a small distance, 0.5 to 1 mm in this example—between the proximal end of the switching cam and the distal end of the blocking window 20 when the blocking element 16 is in engagement with the cavity. As explained further below, this distance is used to generate a haptic or acoustic signal intended to signal that the product has been completely delivered. The small distance z arises from the difference of the distance between the contact surface of the switching cam 17 pointing in the proximal direction and the contact surface pointing in the proximal direction, and the distance between the proximal boundaries of the cavity 18 and the blocking window 20.

Figure 6A:
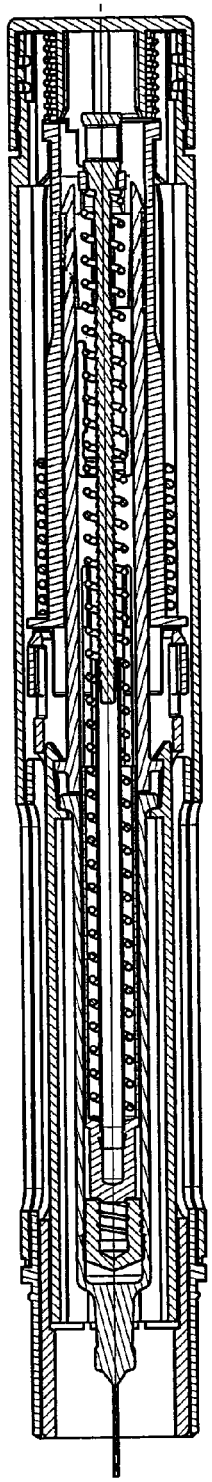
Figure 6B:
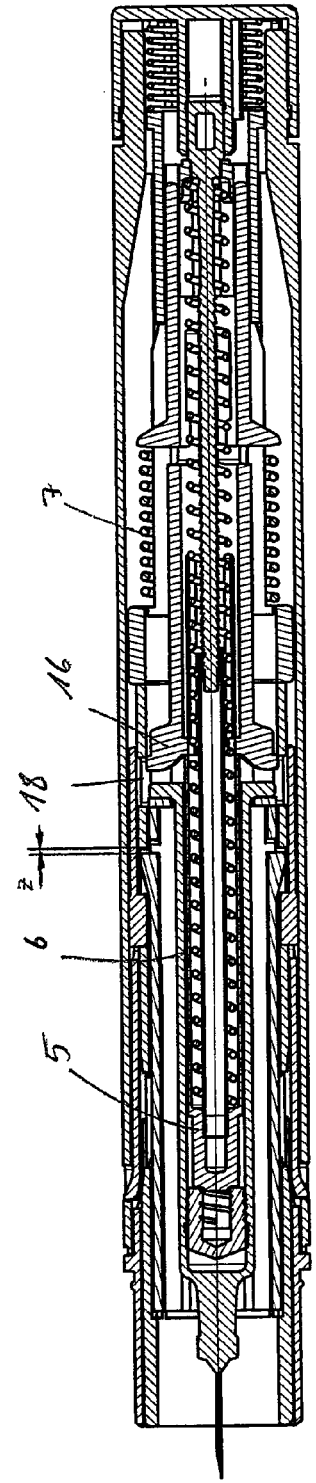

FIGS. 6a and 6b show the injection device in a state after the product has been delivered. While the product is being delivered, the outer circumferential surface of the sleeve-shaped part of the piston rod 5 presses the blocking element 16 into the cavity 18, which secures the blocking element 16 against latching out of the cavity 18 while the product is being delivered. The piston rod 5 can comprise a cavity or its length can be dimensioned such that once the product has been delivered, the securing lock applied to the blocking element 16 by the outer circumferential surface of the piston rod 5 is dropped, such that the blocking element 16 can latch out of the cavity 18, as shown in FIG. 6b, either due to an elastically biased arrangement of the blocking element 16 or due to the geometry of the blocking element 16, which causes the blocking element 16 to be pressed out of the cavity 18.

Figure 7A:
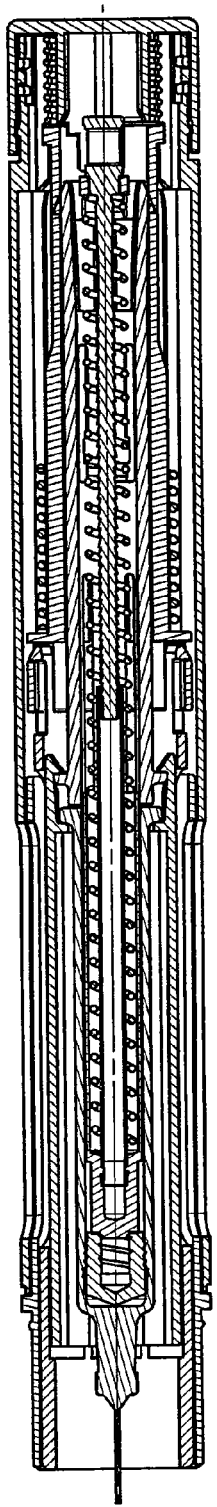
Figure 7B:
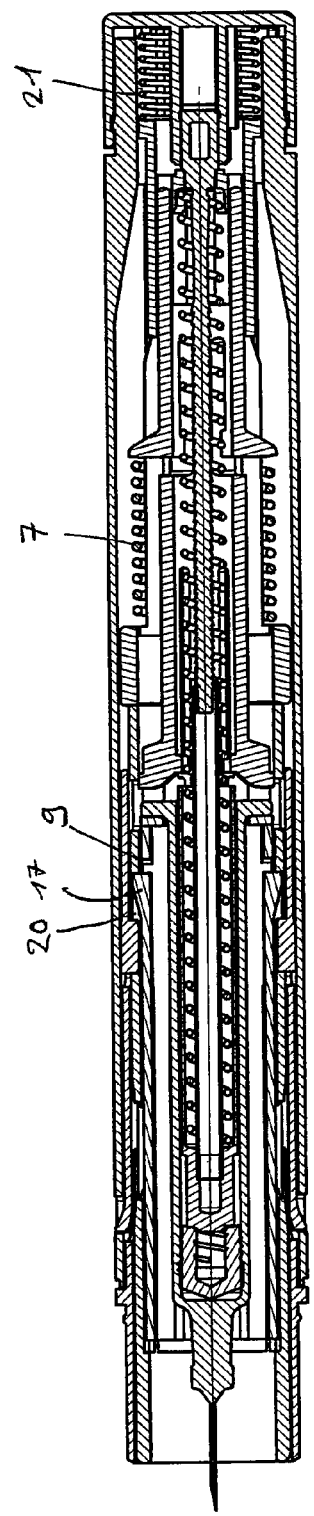
Figure 8A:
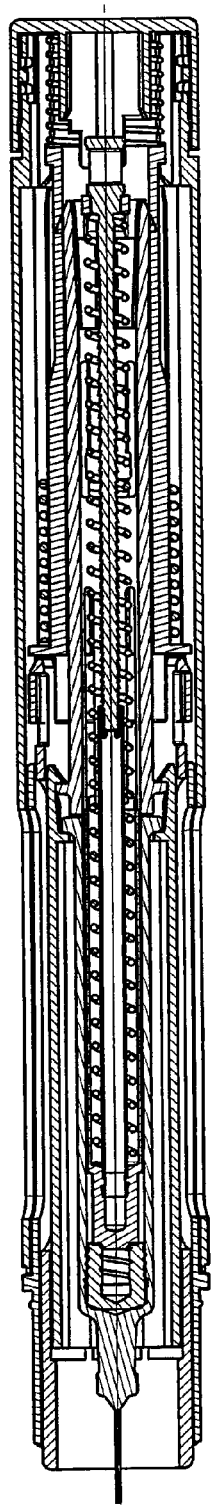
Figure 8B:
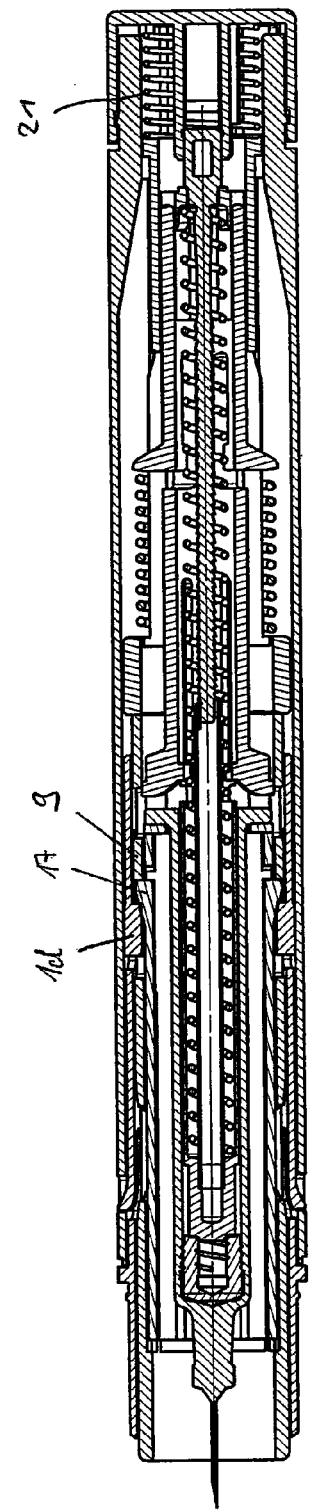

At the end of the product delivery, the advancing spring 6 has been relaxed again, while the tension on the tensed retracting spring 7 has remained constant. The spring force of the advancing spring 6 is then less than the spring force of the biased retracting spring 7. By releasing the engagement between the blocking element 16 and the cavity 18, the retracting spring 7 and the advancing spring 6 are coupled to each other again. As shown in FIGS. 7a and 7b, this coupling causes the small distance z to disappear (see FIGS. 5b and 6b), by moving the proximal end of the advancing structure and/or the switching cam 17, abruptly onto the distal end of the blocking window 20. As the switching cam 17 impacts, a haptic and/or acoustic signal is generated. This movement by the small path z does not yet, however, completely remove the needle 4 from the patient. The patient or user of the device can then wait any length of time before completely removing the needle from the patient, since he can initiate the automatic needle retraction of the device at will.

It is not yet possible to move the needle completely into the distal end of the casing 1, since—as can be seen in FIG. 7b—the switching cam 17 is in engagement with the blocking window 20 and thus blocks or prevents the spring 7 against relaxing. To release the needle 4 for retraction, the user of the device merely has to remove it from the injection location. The restoring spring 21 can then move the operating sleeve 9 in the distal direction via the switch sleeve 8, wherein the advancing structure is fixed relative to the operating sleeve 9, such that the switching cam 17—driven due to its distal design by the spring 21 in conjunction with the operating sleeve 9—is pressed radially inwardly, out of the blocking window 20, by the projection 1d. As soon as the switching cam 17 has been pressed inwardly, the needle 4 is released for retraction. Releasing the engagement also releases the retracting spring 7 for a retracting movement. Due to the greater spring force of the biased retracting spring 7, the entire advancing structure is pressed or urged in the proximal direction, wherein the spring 6 is tensed again and the spring force of the retracting spring 7 is greater than the spring force of the advancing spring 6 during the entire retracting procedure, i.e. up to and including the end of the retracting procedure.

Figure 9A:
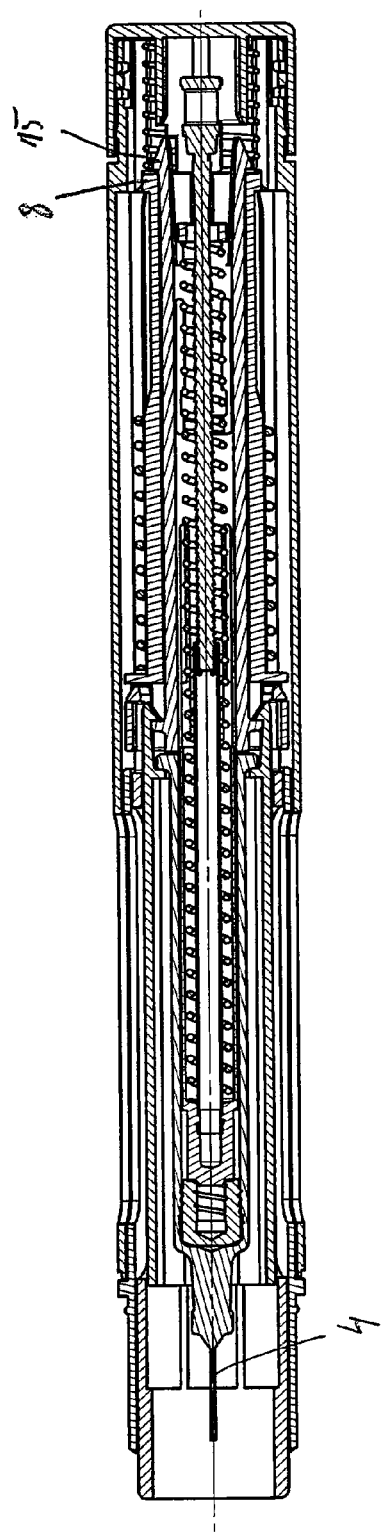
Figure 9B:
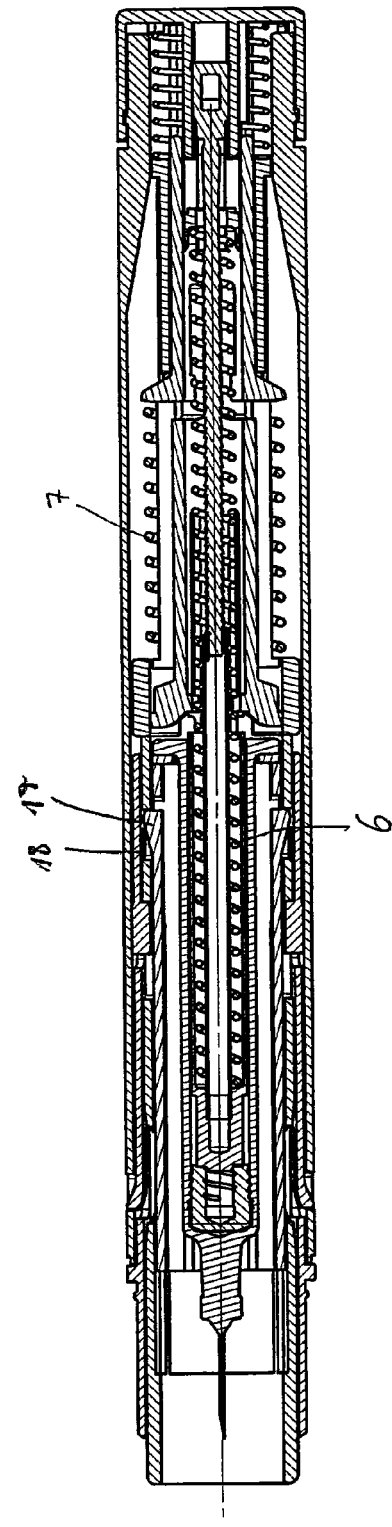

FIGS. 9a and 9b show the injection device in an end state. In this state, the dimensions of the injection device are again the same as at the beginning. Thus, the cap 32 can be fitted again and the injection device disposed of. In the end position, the needle is completely retracted into the distal end of the device. The snapping element 15 is again latched to the switch sleeve 8, as at the beginning. However, it is not possible to trigger the injection device again, since this would require the advancing spring 6 to be biased, as for example shown in FIG. 1a.

Figures 10, 11:
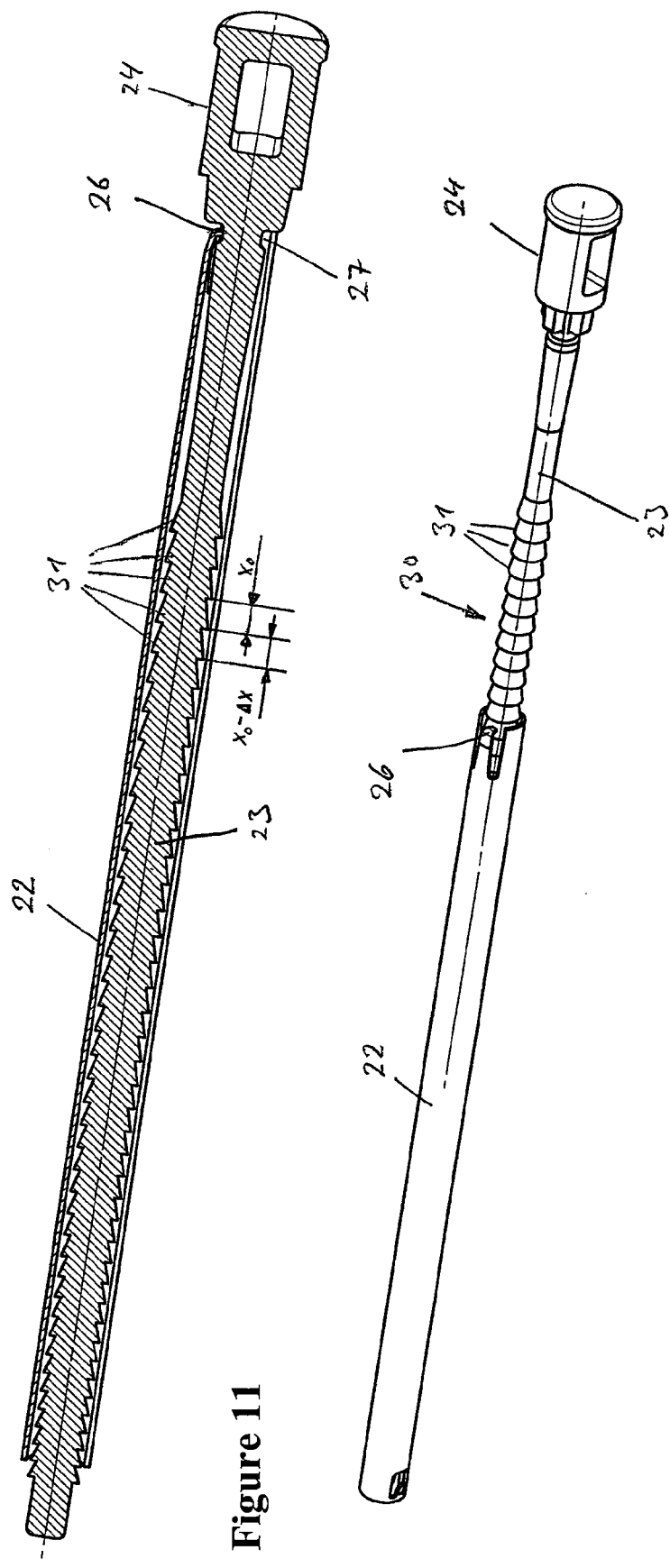
FIG. 10 is a sectional representation of the signalling unit from FIGS. 1 to 9.
FIG. 11 is a perspective view of the signalling unit from FIG. 10.

FIGS. 10 and 11 show in detail the signalling unit of FIGS. 1 to 9. The catch rod 23 comprises a catch 30 comprising a plurality of latching elements 31 arranged along the longitudinal direction at incrementally reduced distances. These distances are reduced as a function of the diminishing spring force. The proximal end and/or the head of the catch rod is connected to the switch sleeve 8 such that it is axially fixed at least in one direction (for example FIG. 1). The catch rod 23 is surrounded by a catch sleeve 22 which is connected to the distal end of the advancing spring 6 or/and to the distal end region of the piston rod 5. The engaging sleeve comprises an engaging element 26 which engages with an annular groove 27. The engaging element 26 engages with the groove 27 in the initial position. During the advancing movement for injecting, i.e. the injection movement, the engaging element latches out of the groove 27 and is moved over a first section of the catch rod up to the beginning of the plurality of latching elements 31. The first section does not comprise any other latching element, but is rather substantially cylindrical or tapered, such that no signals are emitted during the injection movement. The length of the first section is dimensioned such that the engaging element 26 has substantially traveled the whole of the first section once the injection movement is complete. At the start of the delivery movement, the rod 23 and the sleeve 22 are drawn even further apart, such that the engaging element 26 is moved over the second section, i.e. the section with the latching element 31, such that the latching elements 31 are respectively crossed. A brief clicking signal is emitted as each of the latching elements are crossed. The time intervals from one clicking signal to the next are constant, even though the diminishing spring force reduces the speed of the engaging element 26 as the path increases. In accordance with the present invention, the distances from one latching element to the next are reduced as the spring path increases, thus allowing for the varying speed.

On the radially opposite side, on which the engaging element 26 is arranged, another engaging element 26 could be provided. However, in the depicted embodiment, an additional engaging element 26 is not provided, but, as shown here, a support which is formed by the sleeve wall and serves as a thrust bearing.

Figure 12:
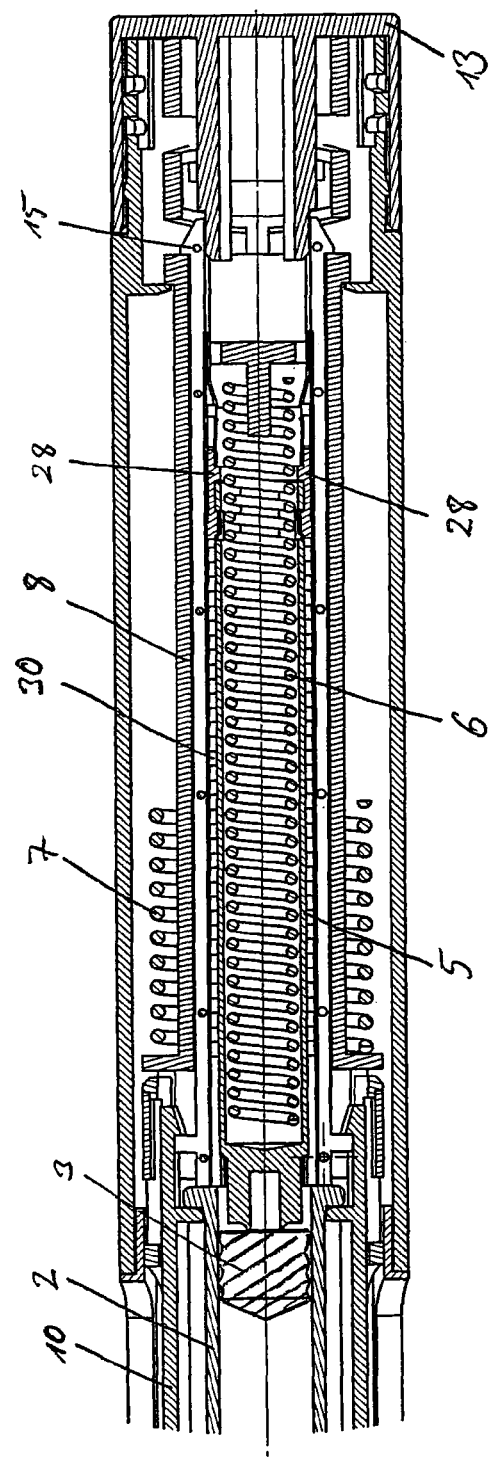
FIG. 12 depicts an embodiment of an injection device in accordance with the present invention, with a different embodiment of a signalling unit.
Figure 13:
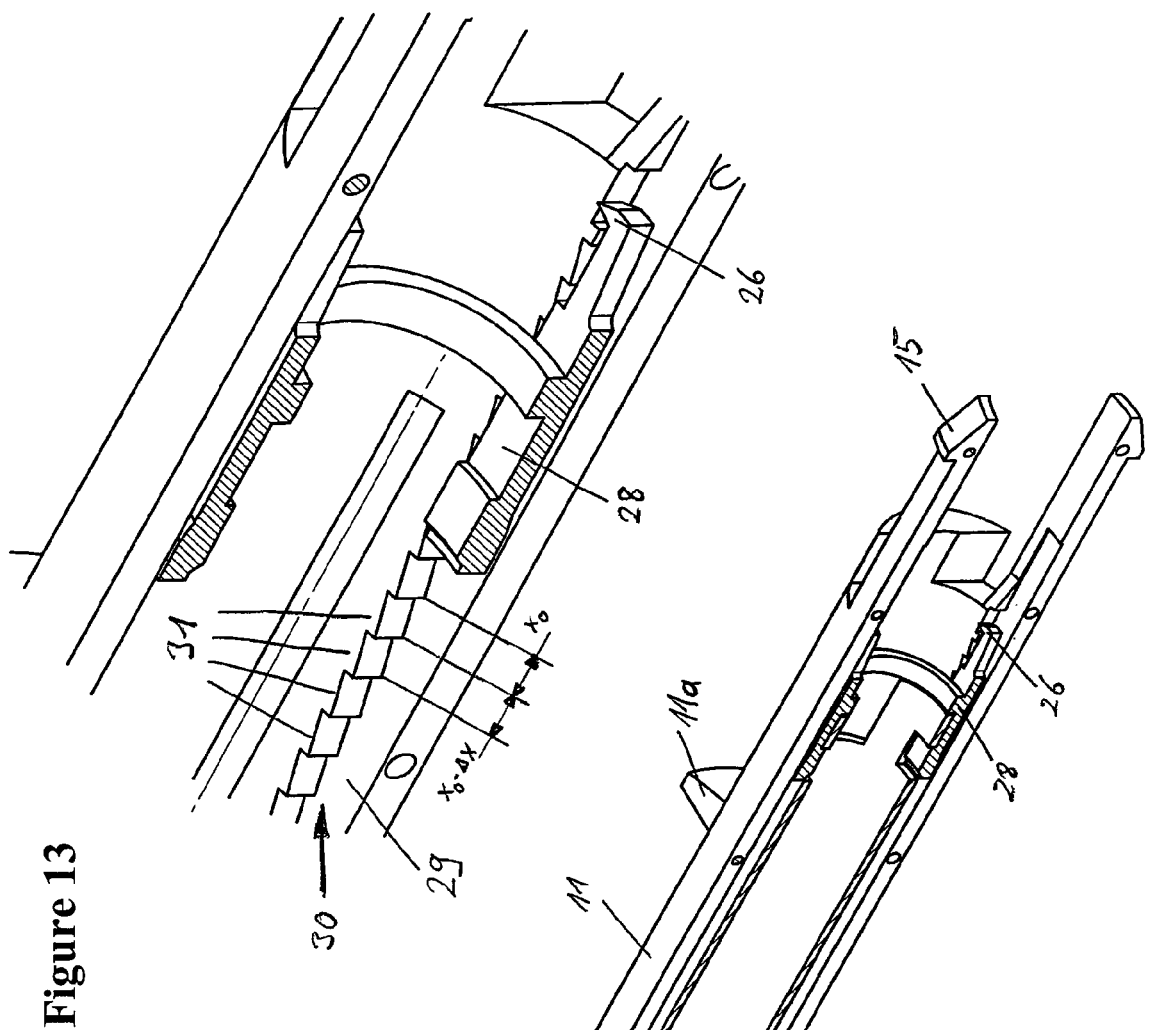
FIG. 13 is a sectional representation of the signalling unit of FIG. 12.
Figure 14:
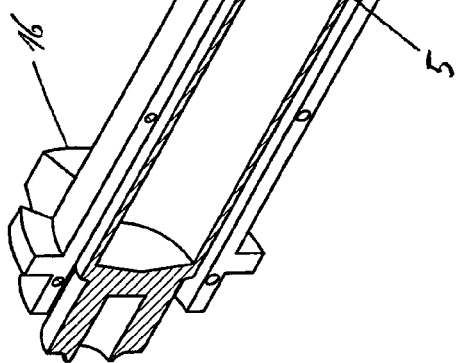
FIG. 14 is another sectional representation of the signalling unit of FIG. 12.

FIGS. 12 to 14 show an alternative embodiment of the signalling unit for the injection device of FIGS. 1 to 9. The catch 30 is arranged in a groove 29, namely on its flank. The latching elements 31 project from the groove flank in the circumferential direction. An axially movable carriage 28 is arranged in the groove 29 and is axially and fixedly coupled to the piston rod 5. During the delivery movement, the carriage 28 is slaved by the piston rod 5, hence the engaging element 26 elastically arranged on the carriage 28 crosses the individual latching elements 31 of the catch 30. Here, too, the latching elements 31 respectively have distances from each other which allow for the varying force of the advancing spring to emit time-constant signals. The distance between the serrated teeth is thus selected such that the individual clicks occur at uniform time intervals, even though the carriage 28 with the piston rod 5 exhibits a lower delivery speed at the end of delivery than at the beginning.

Figure 15:
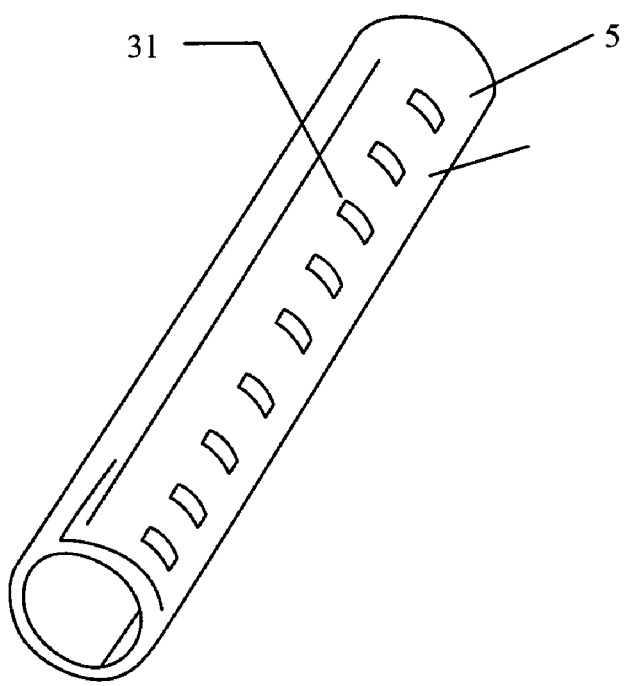
FIGS. 15 and 16 depict another embodiment of a signalling unit in accordance with the present invention.
Figure 16:
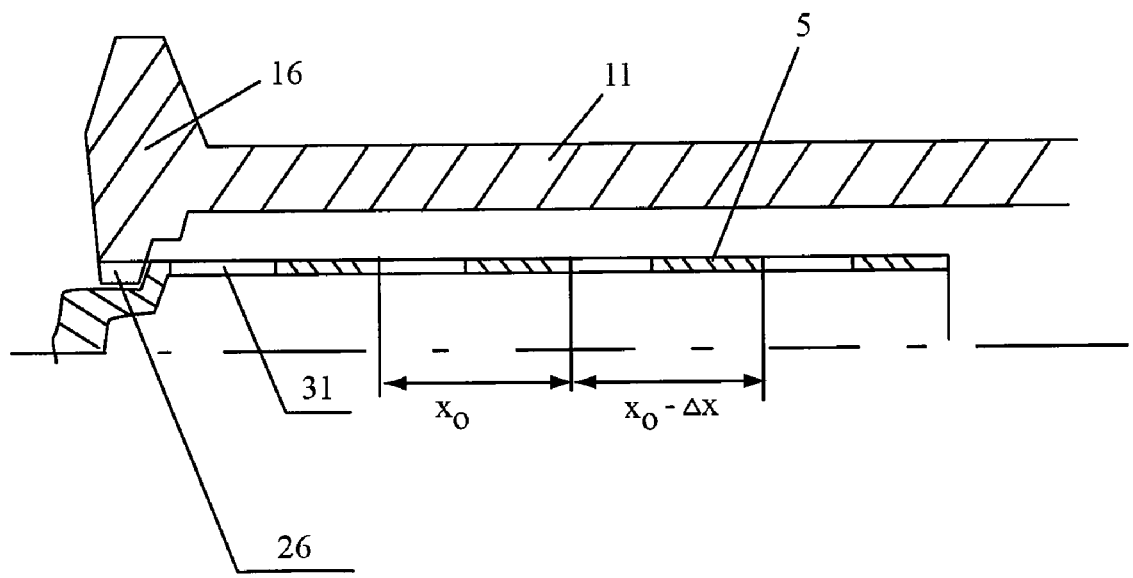

FIGS. 15 and 16 show another embodiment of the signalling unit, in which the catch 30 is formed from cavities, e.g. windows, which are also attached to the piston rod 5 at varying distances. The engaging element 26 is elastically arranged on the functional sleeve 11. During the delivery movement, the piston rod 5 and thus the hole catch 30 are moved past the engaging element 26, which respectively latches into each hole catch 31 and thus generates the signal. The advantage of this embodiment is that the engaging element 26 can be formed by the blocking element 16, such that this embodiment involves few parts.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for administering a liquid product, the device comprising: a drive mechanism for automatically injecting the liquid product, an engaging member and a catch comprising a number of latching elements arranged along a longitudinal axis of the device, wherein at least one of the engaging member and the number of latching elements is relatively moveable to the other along the longitudinal axis to generate a haptic and/or acoustic signal comprising a number of discrete signals due to one of the catch and the engaging member being coupled to the drive mechanism such that the number of discrete signals are generated during an administering movement of the drive mechanism, wherein the drive mechanism generates a variable drive speed during the administering movement, and wherein the latching elements are a variable longitudinal distance from each other that accounts for the variable drive speed such that a time interval between each of the number of discrete signals is constant.

2. The injection device according to claim 1, wherein the variable longitudinal distance is $x_0$; $x_0$-$\Delta x$.

3. The injection device according to claim 1, wherein the haptic and/or acoustic signal is generated during the relative movement.

4. The injection device according to claim 3, wherein the haptic and/or acoustic signal is generated and perceived by a user of the injection device during the relative movement.

5. An injection device for administering a liquid product, comprising:
   a) a catch which comprises at least three longitudinally arranged latching elements; and
   b) an engaging member which can be moved relative to and on the catch along a longitudinal axis of the device and generates a haptic and/or acoustic signal during a relative movement crossing each of the latching elements; wherein
   c) one of the catch and the engaging member is coupled to a drive means for automatically injecting the liquid product, using which generates a variable drive speed during an administering movement of the drive means to generate the relative movement, wherein said relative movement occurs during a single administration; and wherein
   d) the latching elements have a variable longitudinal distance ($x_0$; $x_0$-$\Delta x$) from each other that accounts for the variable drive speed such that the time intervals between the signals are constant.

6. The injection device according to claim 5, wherein the drive means is a spring.

7. The injection device according to claim 5, wherein the drive speed is dependent on a drive force of the drive means which is variable over the movement.

8. The injection device according to claim 5, wherein the drive means is coupled to a piston of a product container, such that the piston can be moved in an advancing direction.

9. The injection device according to claim 8, wherein the piston can be moved, together with the product container, by the drive means in the advancing direction.

10. The injection device according to claim 8, wherein the piston can be moved by the drive means relative to the product container in the advancing direction.

11. The injection device according to claim 5, further comprising an injection needle moveable in the advancing direction by the drive means.

12. The injection device according to claim 5, further comprising a damping element coupled to the drive means such that the drive force of the drive means is damped with a damping action strong enough that creeping occurs.

13. The injection device according to claim 12, said creeping including an aperiodic borderline creep.

14. The injection device according to claim 12, wherein the damping element is formed by the product container with the liquid product contained in it, which can be discharged from the product container via an opening.

15. The injection device according to claim 5, wherein the latching elements comprise at least one of tooth-shaped projections and cavities.

16. The injection device according to claim 5, wherein the engaging member is associated with a carriage which is coupled to the drive means via a piston rod.

17. The injection device according to claim 5, wherein the catch is associated with a functional sleeve surrounding the engaging member.

18. The injection device according to claim 17, wherein the catch is in a groove associated with the sleeve, wherein the latching elements are arranged on a flank of the groove such that the latching elements point in a circumferential direction.

19. The injection device according to claim 5, wherein the catch is arranged on a rod-shaped element surrounded by a sleeve on which the engaging member is formed.

20. The injection device according to claim 19, wherein the latching elements project radially outwardly and the engaging member projects radially inwardly.

21. The injection device according to claim 16, wherein the catch is arranged on the piston rod and the engaging member is arranged on a functional sleeve surrounding the piston rod.

22. A method for generating a haptic and/or acoustic signal in an injection device comprising a drive means, an engaging member and a catch comprising at least three latching elements, the method comprising the steps of:

a) moving one of the engaging member and catch relative to and in contact with the other, the engaging member contacting the at least three latching elements arranged along a longitudinal axis of the injection device during an administering movement of the drive means for automatically injecting a liquid product;

b) using the drive means, coupled to one of the catch and the engaging member, to produce a variable drive speed during the administering movement; and c) generating a haptic and/or acoustic signal whenever the engaging member contacts one of the latching elements, said signal being generated at a constant time interval due to a longitudinal distance from one latching element to another being reduced to account for the variable drive speed.

23. The method of claim 22, wherein said movement occurs during a single injection.

24. The injection device according to claim 1, wherein the drive mechanism comprises a spring and the variable longitudinal distance of the latching elements is a reduced distance from one latching element to the next latching element that accounts for a diminished spring force during the administering movement.

* * * * *